United States Patent [19]
Walters et al.

[11] 4,126,139
[45] Nov. 21, 1978

[54] METHOD AND MEANS FOR RECEIVING PARAMETER CONTROL DATA IN AN IMPLANTABLE HEART PACER

[75] Inventors: Robert A. Walters, Pittsburgh; Steve A. Kolenik, Leechburg, both of Pa.

[73] Assignee: ARCO Medical Products Company, Leechburg, Pa.

[21] Appl. No.: 799,060

[22] Filed: May 20, 1977

[51] Int. Cl.² ............................................. A61N 1/36
[52] U.S. Cl. ............................................. 128/419 PG
[58] Field of Search ...... 128/419 E, 419 PG, 419 PS, 128/419 PT, 419 R, 421, 422, 423

[56] References Cited
U.S. PATENT DOCUMENTS

| | | | |
|---|---|---|---|
| 3,718,909 | 2/1973 | Greatbatch | 128/419 PT |
| 3,727,616 | 4/1973 | Lenzkes | 128/419 E |
| 3,833,005 | 9/1974 | Wingrove | 128/419 PG |
| 4,049,004 | 9/1977 | Walters | 128/419 PG |

*Primary Examiner*—William E. Kamm
*Attorney, Agent, or Firm*—John C. Martin, Jr.

[57] ABSTRACT

A heart pacer employing a digital parameter controlling circuit is controlled by data received from an external source, the data preferably being in the form of magnetic pulses of width corresponding to the desired logic state of the parameter controlling signal. The externally transmitted signal which is received by the pacer comprises both parameter data for controlling selected pacer parameter operation and access data which is processed by the pacer for determining whether the parameter data is accepted for control purposes. The access and parameter data components of the externally generated signal are intermixed so that when receipt of the signal is enabled by the pacer, proper receipt of the parameter data is also ensured.

20 Claims, 6 Drawing Figures

METHOD AND MEANS FOR RECEIVING PARAMETER CONTROL DATA IN AN IMPLANTABLE HEART PACER

BACKGROUND OF THE INVENTION

1. Field of the Invention

This invention relates to implantable cardiac pacers having programmable parameter control and, more particularly, pacers having digital circuitry and improved means for receiving externally generated digital parameter control signals.

2. Description of the Prior Art

In the field of cardiac pacers, as well as other implantable types of biomedical devices, there is an increased appreciation of the role to be played by digital type circuitry. The reasons for this are primarily that the digital technology is a very accomplished technology, and it is well understood that digital technology provides a number of advantages, one of the primary ones being that of efficiency and accuracy of control. In the area of heart pacers, producers have historically preferred simple analog embodiments, for the good and sound reasons that reliability of performance is of utmost concern, and that it is very important to minimize power drain from the battery source. However, with improvements in both digital techniques and means for fabricating very compact, relatively low power drain circuitry, digital embodiments are now being considered more favorably. Another reason for considering digital embodiments in heart pacers is that the batteries, or power sources, are now much improved, and the slightly higher power drain of digital circuitry can be more readily tolerated.

The patent literature has for some years now disclosed digital forms of cardiac pacers as well as means for programming same by the pickup of an externally generated program signal. U.S. Pat. Nos. 3,805,796 and 3,833,005 are representative of the prior art. However, the known prior art has a number of shortcomings in the area of reliably introducing parameter control data to an implanted pacer. For example, in prior art arrangements, the externally generated parameter signal, assuming it is accurately received, must be converted after it has been received so as to be in a proper logic form for control of the pacer circuitry. Likewise, in prior art arrangements, the accessing or "addressing" of the pacer is conducted independently of the receipt of the parameter data, such that even though the pacer is reliably isolated from being mistakenly re-programmed by unwanted signals and/or interference, there is no control over ensuring accurate data input after the access has been gained. In other words, even after access has been gained, interference could be present which would cause improper parameter data input to the pacer, or the pacer circuitry itself could improperly receive and/or decode the parameter data from the external source. The prior art has thus retained the problem of properly inputting data to an implanted pacer, especially the problem of reliably inputting a digital data word which is in form for direct parameter control.

SUMMARY OF THE INVENTION

It is a primary object of this invention to provide a cardiac pacer having means for receiving an externally generated binary data word, which means provides an increased security of properly receiving all of the parameter control data in the binary word.

It is another object of this invention to provide, in a cardiac pacer, a method and means for receiving parameter control data in digital form, and for doing so with a minimum number of received data bits, while increasing the reliability and simplifying the pacer circuitry for accomplishing such receipt.

It is another object of this invention to provide, in a digital pacer, circuitry for receiving externally generated parameter control data, wherein said received data is self-checked after receipt in the pacer.

It is yet another object of this invention to provide a method and means for receiving data in an implantable heart pacer, wherein said data is in the form of a data word containing intermixed access and parameter data, whereby proper accessing of the pacer also ensures proper parameter data receipt.

It is another object of the invention to provide heart pacer parameter control circuitry which receives an externally generated multiple bit data word, in which the bit data is determined by the width of the respective pulses of the received data word.

In view of the above going objects, the invention presents a pacer circuit for providing parameter control logic states for control of respective different parameters of the pacer. The circuit includes means for receiving a data word made up of a plurality of pulses of selected widths which are generated and applied externally from the patient. In a first embodiment, means are provided in the pacer for comparing predetermined bits of the data word with corresponding other bits of the word, for the purpose of permitting use of the parameter data for control purposes only upon determination that the entire data word has been properly received. In another embodiment, a stored access data circuit is utilized, and selected access bits which are intermixed with parameter bits in the binary data word are compared with corresponding bits (or logic states) of the stored access data, whereby entry of the parameter control data for control purposes is enabled only upon a positive comparison. In yet another embodiment, features of both of the above embodiments are incorporated in a hybrid arrangement.

DETAILED DESCRIPTION OF THE PREFERRED EMBODIMENTS

Figure 1:
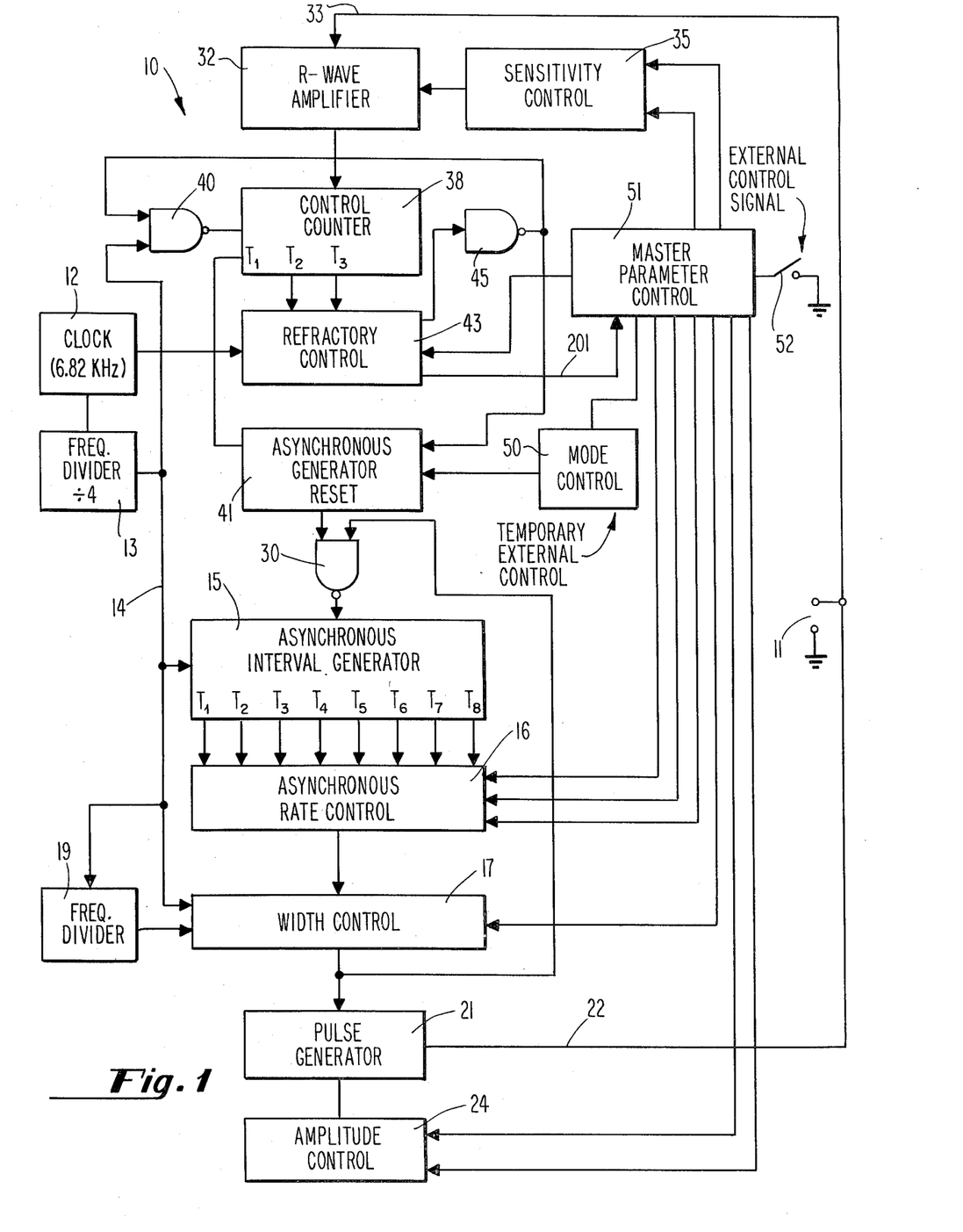
FIG. 1 is an overall block diagram of the heart pacer of this invention, which includes a parameter control circuit and means for receiving an externally generated parameter control signal.

The cardiac pacer, in accordance with a preferred embodiment of the invention is shown in block diagram form in FIG. 1, and is denoted generally by the reference numeral 10. (The various specific electrical circuits of the cardiac pacer in FIG. 1 are illustrated and described below in detail.)

With reference now to FIG. 1, the cardiac pacer 10 receives naturally produced cardiac and other signals from, and supplies stimulation signals to, terminals 11, adapted to be connected to heart electrodes, such connections being well known in the art.

The cardiac pacer 10 operates in conjunction with a digital clock 12, which supplies clock pulses at a frequency of, for example, 6.82 KHz. Pulses from the clock 12 are divided by a frequency divider 13 to be supplied on line 14 to an asynchronous interval generator 15. The asynchronous interval generator 15 has a plurality of outputs T1–T8 each connected to a respective input of an asynchronous rate control circuit 16. Each of the outputs T1–T8 represents a different asynchronous interval within the range of interest, and the asynchronous rate control 16 selects one of the outputs T1–T8 from the asynchronous interval generator 15, as controlled by a master parameter control circuit 51, below particularly described.

The selected output from the asynchronous interval generator 15 is conducted to a width control circuit 17, which produces an output pulse of selected width, as controlled by the master paremeter control 51. This capability is enabled by the clock pulses upon the line 14 which are inverted at inverter 18 and then applied to the width control 17 and to a frequency divider 19, which produces additional clock pulses at a submultiple of the frequency of the clock 12, for application to the width control circuit 17, thereby providing two clock pulse frequencies from which the various widths of the output pulse can be controlled.

The output pulses from the width control circuit 17 are applied to trigger a pulse generator 21 to produce an output pulse upon output line 22 for delivery to the terminals 11. The amplitude of the pulse generated by the pulse generator 21 is controlled by an amplitude control circuit 24, which, in turn, is also controlled by the master parameter control circuit 51.

The output of the width control circuit 17, in addition to its connection to the pulse generator 21, is conducted via a NAND gate 30 to a resetting terminal of the asynchronous interval generator 15. Thus, when the asynchronous generator 15 reaches a predetermined selected count and produces an output pulse, and the width control circuit 17 generates an output, the asynchronous interval generator is reset to begin counting a subsequent asynchronous interval.

The portion of the cardiac pacer thus described serves as a so-called "fixed rate" pacer, producing pulses asynchronously at a rate controlled by the selected output of the asynchronous interval generator 15. To provide a "demand" pacer capability, a heart signal responsive resetting circuit is provided. This resetting circuit includes an R-wave amplifier 32 having an input connection to terminals 11 from which naturally occurring heart pulses are conducted upon line 33. Other signals, such as stimulation pulses produced by the pulse generator 21 upon the line 22, and electromagnetic interferring noise as may be detected by the heart electrodes or other associated circuitry may also be detected upon the line 33, but is filtered or rejected or initiates an interference or fixed rate mode, as will become apparent below. The sensitivity of the R-wave amplifier 32 is controlled by a sensitivity control circuit 35, which, in turn, is controlled by the master parameter control 51.

The R-wave amplifier 32 produces an output signal upon the detection of a naturally produced R-wave, a stimulation pulse, or an interference signal, for delivery to a control counter 38. The control counter 38 also receives clock pulses from the clock pulse frequency divider 13 via a NAND gate 40, and produces outputs at times $T_1$, $T_2$ and $T_3$, respectively after being reset. The output generated at time $T_1$ is conducted to an asynchronous generator reset circuit 41 which produces an output delivered via NAND gate 30 to reset the count of the asynchronous interval generator 15. Thus, in operation, if an R-wave, a stimulation pulse, or an interference signal is received by the R-wave amplifier 32 prior to the time which a signal appears on a selected output of the asynchronous interval generator 15, the asynchronous interval generator 15 is reset to begin its count anew, in a fashion known in the art as demand operation.

In addition, one of the other of the outputs $T_2$ or $T_3$ of the control counter is selected by a refractory control circuit 43, as controlled by the master parameter circuit 51. The selected output $T_2$ or $T_3$ is connected to an inverting NAND gate 45, for application to the NAND gate 40 controlling the passage of the clock pulses upon the line 14, and to the asynchronous generator reset circuit 41 to produce a state therein allowing the passage of a subsequently produced asynchronous generator reset pulse from the control counter 38. Thus, the refractory circuit functions to produce an "alert state" within the asynchronous generator reset circuit 41 after the control counter 38 has reached a predetermined refractory count determined by the refractory control circuit 43. Upon producing the alert state, a logic state is applied to the input of the NAND gate 40 disabling the passage of the clock pulses upon the line 14, terminating the counting by the control counter 38. Thereafter, the production of an output by the R-wave amplifier 32 produces a pulse resetting the control counter 38 and enabling it to begin its count again. When the count has reached time $T_1$, the asynchronous generator reset 41, previously enabled by the refractory control circuit 43, produces a reset pulse to reset the count of the asynchronous interval generator. Prior to the reaching of the "alert state", however, the pacer is in a "control state" during which the reception of a signal from the R-wave amplifier 32 does not produce an asynchronous interval generator resetting pulse. Instead, the control counter 38 is merely reset to count the preselected refractory period from the beginning.

In addition, a mode control circuit 50 is provided which is controlled by the master parameter control 51. The mode control circuit 50, when operated, disables the operation of the asynchronous generator reset circuit 41, to thereby cause the pacer circuit 10 to operate in a fixed rate mode. Additionally, the mode control 50 can be operated by a temporary external control, such as an electromagnet or the like, to cause the circuit to operate in a fixed rate mode for testing purposes, as is well known in the art.

The master parameter control 51, below described in detail, is programmed via an external control signal applied to a receiving element 52, such as a magnetically activated reed switch or the like, as below described.

As indicated, the cardiac pacer 10, in accordance with the present invention, includes a facility for varying its operating parameters; more particularly, the stimulation pulse width, the stimulation pulse amplitude, the refractory period, the heart signal sensitivity, the mode (i.e., fixed rate or demand) and the asynchronous pulse generation rate. These operating parameters, furthermore, can be varied after the pacer has been implanted into the body of the patient. To facilitate this parameter controlability, the master parameter control circut 51 is employed.

As will become apparent, the master parameter control circuit 51 is responsive to an externally applied input from an instruction device or transmitter, such as described in copending application Ser. No. 686,255, now abandoned which is incorporated by reference. The instruction device provides a sequence of electromagnetic pulses which includes both parameter data and access data, as is detailed below. The control circuit 51 must recognize the access data before the parameter data will be acted upon for control of the operating parameters of the pacer.

Figure 2:
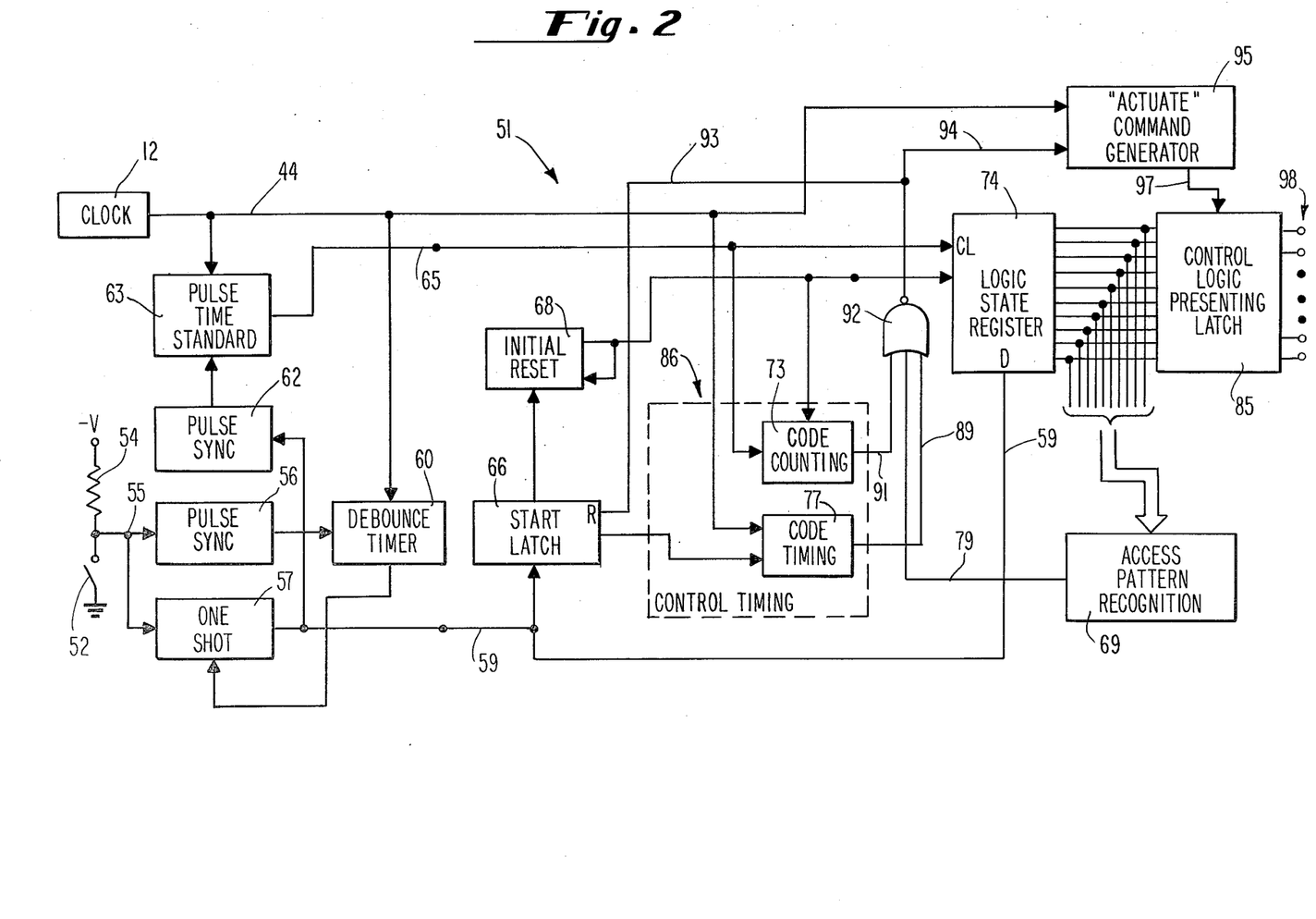
FIG. 2 is a block diagram of the parameter control circuit of this invention.

More particularly, with reference now to FIG. 2, the master parameter control circuit 51 derives pulses from the clock 12 upon the line 44 to enable the moving and processing of the various pulses and logic states through the master parameter control circuit.

The externally generated and transmitted magnetic pulse are received upon a magnetically actuated reed switch 52. The reed switch 52 is connected in series with a resistor 54 to a low state whereby when the reed switch 52 is closed, pulses are developed across the resistor 54, causing the state upon the input line 55 to change from low to high (ground) state.

The data input line 55 is connected to a pulse sync circuit 56 and to a digital one-shot pulse generator 57. The output of the one-shot pulse generator 57 is controlled by a debounce timing circuit 60, and is developed upon output data line 59. The debounce timer 60 is actuated by the output from the pulse synchronizing circuit 56 and is controlled by the clock pulses delivered upon line 44. In essence, the debounce timer circuit is a delay circuit which permits the passage of pulses by the one-shot generator 57 only after the expiration of a sufficient time for the magnetic reed switch 52 to complete whatever bouncing it goes through upon closing. The pulses developed upon the data line 59 represent the pulses produced at the magnetic reed switch 52, except delayed at the start by the action of the debounce timer circuit 60. The pulses on line 59 are terminated at the end of the pulses at line 55.

The output from the one-shot pulse generator 57 upon the data line 59 is delivered to a second pulse synchronizing circuit 62 after which it is conducted to a pulse-time-standard generator 63. The pulse-time-standard generating circuit 63 functions to produce timing pulses a predetermined time after the occurrence of each of the data pulses produced upon the data line 59. The pulses produced by the pulse-time-standard circuit 63 upon the output line 65 serve two purposes. Briefly, the first purpose is to enable the data pulse upon the line 59 to be characterized as a "0" or "1" logic state. The second purpose is to provide a signal indicating that a data pulse has been received to permit the data pulses to be counted to insure that the various operating parameters of the pacer are not changed until after all of the transmitted pulses are in fact received.

Upon the appearance of the first data pulse upon the data pulse line 59, a start latch circuit 66 is activated. The start latch circuit 66 activates an initial reset circuit 68, which initializes to a beginning state the code counting circuit 73 and the logic state register 74. The start latch 66 additionally initiates the code timing circuit 77. Start latch 66 is reset by a signal on line 93, following the end of the external signal.

The data pulses upon the data line 59 are applied to a data ("D") input of shift register 74 and the pulse-time-standard pulses appearing on the line 65 are applied to a clock ("CL") input of the register 74. As above mentioned, the pulses from the pulse-time-standard circuit 63 appear at a predetermined time after the leading edge of the data pulses. Thus, if the data pulse is in a high state at the time the pulse-time-standard pulse appears at the clock input to the register 74, a logic "1" will be entered. If, however, the data pulse has terminated prior to the initiation of the pulse-time-standard pulse, a logic "0" will be registered in the register. Since the pulse output from one-shot 57 terminates concurrently with the end of the received pulse, a logic "1" or "0" will be sensed depending upon the time width of the external pulses. Thus, by coding the external signals in 2 widths, e.g., 5 MS and 15 MS, means is provided for detecting the pulse as a "1" or "0". For example, if the predetermined time delay of circuit 63 is 10 MS, the 5 MS signal is sensed as a "0", and the 15 MS signal is sensed as a "1". Thus, the data pulses upon the line 59 are registered in the logic state register 74 as a logic "0" or a logic "1" state depending on their concurrence with the pulse-time-standard pulses upon the line 65. Upon the completion of the data transmission, and assuming access pattern recognition as described below, the logic states within the logic state register 74 are moved to the control logic presenting latch 85 to control the operation parameters of the pacer with which the master parameter control 51 circuit is associated.

Timing of the incoming data pulses is provided by the control timing circuitry 86. The control timing circuitry includes means for timing the overall code, as well as means for counting the number of magnetic pulses received. Thus, a code timing circuit 77 is provided which is initiated by the start latch 66 to receive and count clock pulses upon the line 44 to provide an output upon its output line 89 after a predetermined time within the entire sequence of magnetic pulses (including both the access data and parameter data) should be received.

Additionally, the pulse-time-standard pulses upon the line 65 are applied to the code counting circuit 73, which provides an output upon its output line 91 after a number of pulses corresponding to the total desired number of pulses are received.

The output lines 89 and 91 are connected to the inputs of a NAND gate 92, which produces a state change (to a low state) upon the output line 94 thereof only upon the concurrence of high states upon its input upon lines 79, 89 and 91. The output of the NAND gate 92 is connected to the "actuate" command generator circuit 95 to produce a pulse upon its output line 97 to the control logic presenting latch 85. Thus, in operation, as the data pulses are registered as logic states of 0 and 1 into the logic state register 74, the code counting circuit 73 and code timing circuit 77 are operating. Assuming that a proper access pattern has been recognized by circuit 69, line 79 is high. When the desired requisite number of pulses are counted, line 91 is high, and after the predetermined time line 89 is also high, producing an enabling signal on line 94. The "actuate" command generator 95 is then activated to present a signal upon the output line 97 to transfer the logic states within the logic state register 74 to the control logic presenting latch 85. The logic states, therefore, are then presented upon the various output terminals 98 of the control logic presenting latch 85 to be operational to vary the parameters of the heart pacer with which the master parameter control circuit 51 is associated. In practice, respective output terminals 98 are preferably connected directly to control blocks 16, 17 and 24, since the binary word which has been received from the external source is arranged so that when the parameter data has been entered in the latch 85 the respective logic states can be used directly for parameter control. However, if the received word is not already in proper binary form for use in parameter control, terminals 98 may be connected to decoder circuitry (not shown) for generation of logic signals for connection to the various control circuits.

Figure 3:
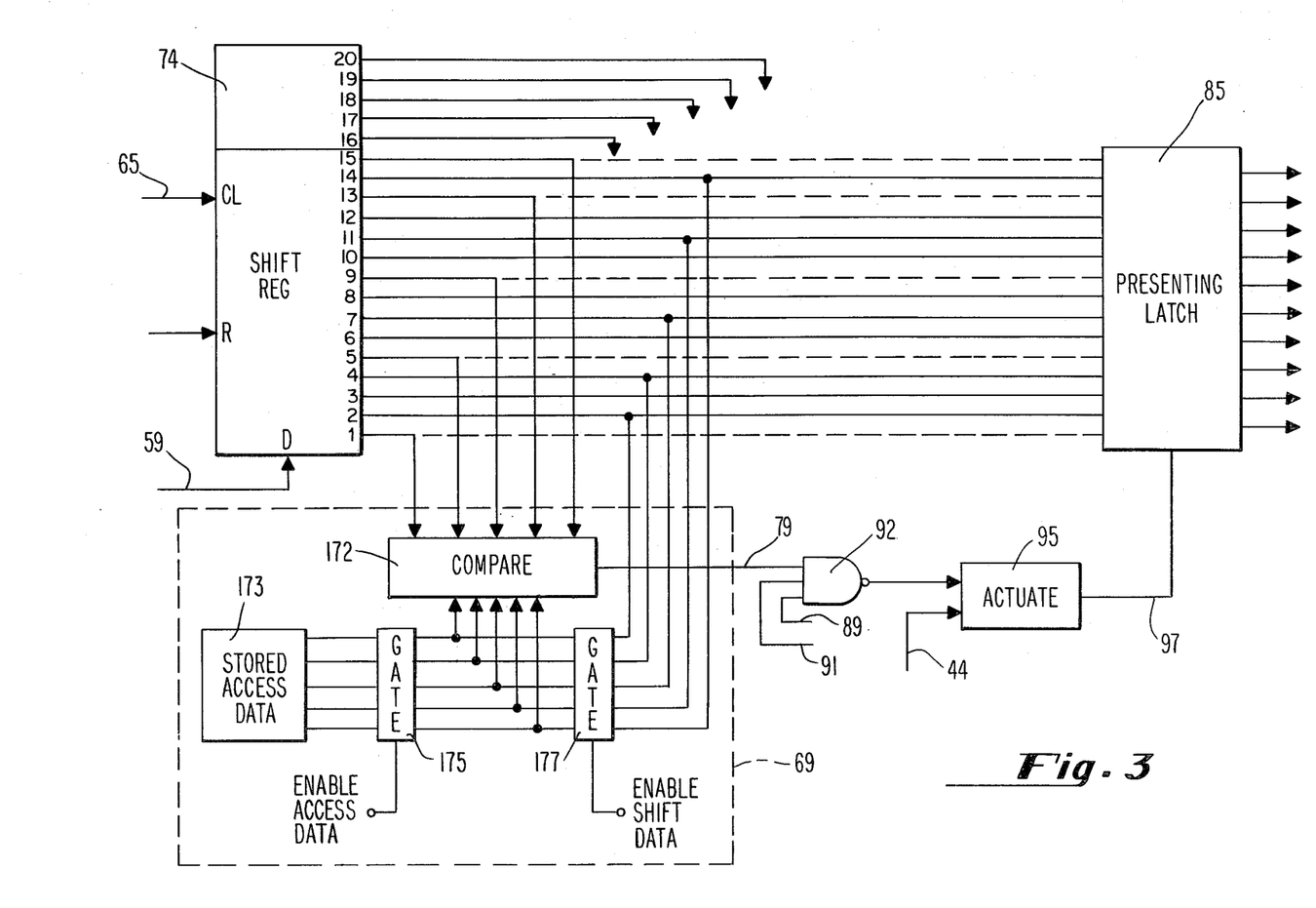
FIG. 3 is a detailed block diagram of the pacer circuitry for determining whether an external signal is to be accepted for purposes of parameter control.

Referring now to FIG. 3, register 74 receives clock pulses from line 65 which correspond to each received pulse transmitted from the external source. The first pulse of the data word also produces an output from reset circuit 68, which is connected into the R terminal of shift register 74 to reset the register. Subsequent pulses on line 65 carry entry of a 0 or a 1 as discussed above, and shifting of the information through the register. Th register may have any desired number of stages, but as illustrated it is shown to have 20 stages for storage of 20 logic states or 20 bits. If the external binary word, which is received thrugh receiving element 52 contains 15 bits (both parameter and access bits), then only 15 stages are utilized. On the other hand, if it is desired to have the binary word contain 20 bits, then of course all 20 stages are utilized. In the discussion corresponding to FIGS. 4-5 below, illustrations are presented wherein either 15 bit words or 20 bit words are employed.

Register 74 has an output line shown connected to each of the stages of the register. The output lines are connected both to access pattern recognition block 69 and to the presenting latch 85, although the matrix of connections does depend upon the nature of the encoding of access and parameter data within the binary word. Access pattern recognition block 69 contains a comparison circuit 172, which receives inputs both from predetermined ones of the shift register output lines and from either gate 175 or 177. Stored access data circuit 173 is a read only memory circuit, which contains predetermined data in the form of a unique access code or "address" for the pacer. In the embodiment where the stored access data is to be utilized, this data is gated through gate 175 and connected as a set of inputs to compare circuit 172. Alternatively, given ones of the outputs from register 74 may be connected through gate 177 to provide a set of input data to compare circuit 172. By whichever arrangement, compare circuit 172 receives a first set of data directly from register 74, and a second set of data either from circuit 173 or from other shift register output lines. If corresponding bits from each set compare to be the same, an output is produced on line 79 to gate 92. When all of the input logic conditions at gate 92 are met, including the enabling signal from compare circuit 172, a signal is sent to actuate circuit 95 which in turn delivers an actuating signal on line 97 to the presenting latch 85.

As illustrated in FIG. 3, logic states 1, 5, 9, 13 and 15 of register 74 are shown connected directly to compare circuit 172, these connections comprising a first set of input data to the compare circuit. In an embodiment employing the stored access data circuit 173, the five logic states of circuit 173 are connected to corresponding second inputs of compare circuit 172. Compare circuit 172 then compares the corresponding sets, and produces an output signal when and only when the logic states 1, 5, 9, 13 and 15 of register 74 compare to the stored access data of circuit 173. Alternatively, the embodiment may not utilize stored access data, but may take comparison data from, by way of example, logic states 2, 4, 7, 11 and 14 as illustrated, to provide the second set of comparison data. Although FIG. 3 illustrates gates 175 and 177, either one of which may be enabled so as to effectuate a choice of comparison, in practice, a pacer designed according to this invention for implanation preferably employs only one of the illustrated embodiments, in which case the gates are not necessary, and the comparison data is simply directly connected to the compare circuit 172.

Figure 4:
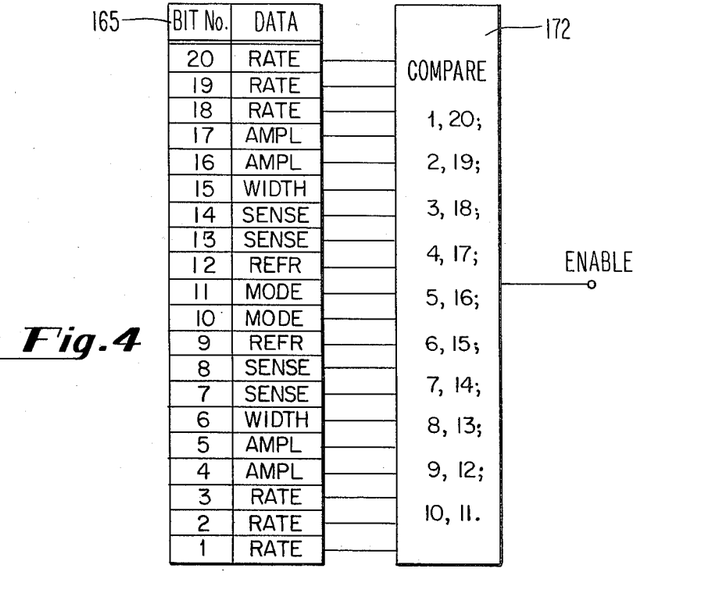
FIG. 4 is a representation of the binary word used in a first embodiment of this invention, and the data comparison made by the pacer prior to acceptance of the word for purposes of parameter control.
Figure 5:
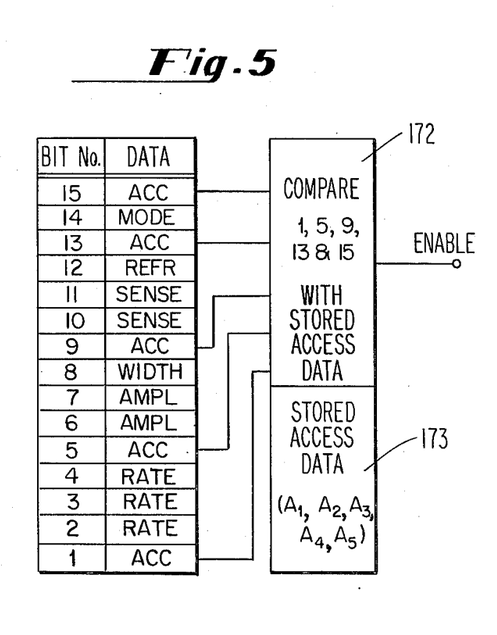
FIG. 5 is a representation of the binary word used in a second embodiment of the invention, and the data comparison made by the pacer prior to acceptance of the word for purposes of parameter control.
Figure 6:
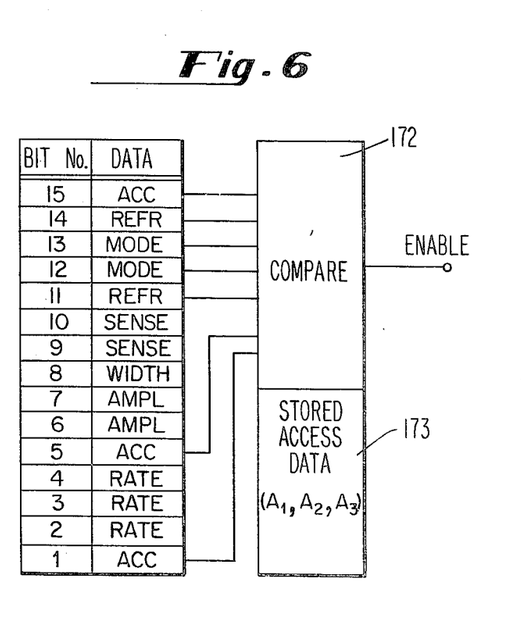
FIG. 6 is a representation of the binary word used in a third embodiment of this invention, and the data comparison made by the pacer prior to acceptance of the word for purposes of parameter control.

Referring now to FIGS. 4 through 6 along with FIG. 3, there are illustrated several embodiments of the basic arrangement of this invention. The block designated 165 of FIG. 4 illustrates the arrangement of the data bits which are fed into register 74, register 74 in this case containing 20 stages corresponding to 20 logic states. A 20 bit word is utilized in this embodiment, having 10 parameter bits and an additional 10 bits containing the same information in mirror form. By way of example, the first 3 bits, corresponding to logic states 1, 2 and 3 of register 74, contain information to be used for setting the pacer rate. (Note that in FIG. 1, there are 3 lines coming from master control block 51 into asynchronous rate control block 16.) Bits 20, 19 and 18 of the externally generated binary word contain corresponding data, i.e., bit 20 is the same as bit 1, bit 19 is the same as bit 2, and bit 18 is the same as bit 3. When and if the binary word has been properly entered into register 74, the comparison of logic states 1 and 20, 2 and 19, and 3 and 18, as performed in compare circuit 172, should be positive, meaning that the data has been entered properly. Correspondingly, amplitude bits 4 and 5 are mirrored by bits 17 and 16; width bit 6 is mirrored by bit 15 of the binary word; sense bits 7 and 8 are mirrored by bits 14 and 13 respectively; reference bit 9 is mirrored by bit 12; and mode bit 10 is mirrored by bit 11. Thus, in this embodiment, the 10 comparisons indicated at block 172 of FIG. 4 are performed in circuit 172, and only if all 10 comparisons check out is the enable signal generated and transmitted on line 79. With reference to FIG. 3, connections are made from outputs 11-20 to the lower side of compare circuit 172, and connections from output stages 1-10 are made to the upper side of compare block 172.

The embodiment of FIG. 4 contains the advantage that all of the bits of the externally generated binary word must be properly entered into the receiving portion of the pacer. If any one or more of the bits of the word are not properly shifted through, the comparison will prove negative, and no enable signal will be conducted to presenting latch 85. In other words, if there is any noise interference, or if the operation of any portion of the overall master parameter control 51 is faulty such that the bits are not properly inputted, then the new parameter data is not presented to the pacer. Note that this is an improvement over the prior art arrangement where the pacer is simply first addressed by any conventional means, such as the inputting of an address code, and upon proper addressing the remaining parameter data is inputted. In that prior art arrangement, even though the pacer may be properly addressed, there could be error somewhere in the subsequent inputting of the parameter data to the pacer, which error would not be detected. However, this arrangement is fail safe in that both the "addressing" and introducing of the parameter data are carried on simultaneously such that when the data is accepted it is known to have been accepted properly.

Referring now to FIG. 5, there is shown another embodiment of applicant's invention utilizing a 15 bit externally generated binary word, and also utilizing stored access data circuit 173. In this arrangement, access, or address data is arranged in 5 separate bits which are intermixed as bits 1, 5, 9, 13 and 15. The parameter data is contained in the other 10 bits of the 15 bit word. In other words, the access data is interspersed within the overall binary word. Compare circuit 172 receives inputs from logic states 1, 5, 9, 13 and 15 and compares these respectively with 5 logic states $A_1 - A_5$ from stored access data circuit 173, and upon a positive comparison generates the enable signal on line 79.

Referring now to FIG. 6, there is shown a hybrid arrangement which incorporates features of the arrangements of FIG. 4 and FIG. 5. In this embodiment, which is also illustrated as utilizing a 15 bit binary word, access data is encoded only in bits 1, 5 and 15. Outputs from logic states 1, 5 and 15 of register 74 are compared with stored access data $A_1 - A_3$. At the same time, reference bit 11 is mirrored by bit 14, and mode bit 12 is mirrored by bit 13, and circuit 172 also compares bits 11 and 14, and 12 and 13. For this arrangement, the following positive comparisons must be made in order to generate an enable signal on line 79:

Bit 1 must correspond to $A_1$ stored in circuit 173; bit 5 must compare with $A_2$ stored in circuit 173; bit 15 must compare with $A_3$ stored in circuit 173; bit 11 must compare with bit 14; and bit 12 must compare with bit 13.

From the embodiments illustrated, it is seen that a great deal of flexibility can be incorporated, and various hybrid arrangements may be made within the scope of this invention, as a matter of choice. Where a 15 bit binary word is used, it can be arranged so that any five of the parameter bits may be compared with 5 other bits. As illustrated in FIG. 3, bits 1, 5, 9, 13 and 15 may be compared with bits 2, 4, 7, 11 and 14. It is obvious that any other arbitrary arrangement may be utilized. Also, although the invention has been illustrated in terms of 15 and/or 20 bit words, it is clear that the binary word may contain any desired number of parameter bits and access (or comparison) bits, as desired. The advantages of the invention are derived from the randomness of the spacing of the access bits, which increases the security of proper entry of parameter data insasmuch as entry is not enabled unless the required comparison is made, and the comparison will not be achieved unless all of the bits, including the parameter bits, are properly entered. By having access or comparison bits at or near both the beginning and the end of the word, proper feedthrough of the parameter bits is ensured.

The invention has been specifically illustrated as incorporating a receiving element 52 such as a magnetically activated read switch or the like. However, the invention is understood to embrace any manner of coupling the externally generated signals into the pacer. Likewise, in the preferred embodiment the logic states of the externally generated signals are determined by the width of each pulse component of the externally generated signal but the invention embraces other means for encoding the externally generated signals.

As claimed herein, the invention utilizes a data word which is externally generated by any conventional generating equipment. The data word comprises both parameter data and access, or comparison data. By parameter data is meant bits of information which are used to actually control parameters of the pacer. The terms access data and comparison data are used interchangeably, and relate to that portion of the total externally generated signal, or word, which is used in the pacer for the purpose of making a check to see whether the signal should be accepted for control purposes. The data in the external signal is preferably encoded in a time sequence such that successive bits of information may be fed directly into a shift register, such that after the external signal, or word, has been entirely loaded into the register, the logic states of the register correspond to the time sequence of the bit information of the received signal. In referring to the register, the terms "data locations" and "logic states" are used interchangeably. Of course, when the register is a binary register, each data location or logic state represents a separate bit of the entire binary data word. There may be any predetermined number "n" of logic states in the register, and likewise there may be any number of bits of data, parameter and/or access, in the transmitted and received data word.

We claim:

1. An implantable cardiac pacer adapted for connection to electrode means for delivering stimulus signals to and receiving signals from a human heart, and being further adapted to be programmed according to an external signal comprising intermixed parameter data and access data transmitted serially to said pacer, comprising:

demand generator means having an output adapted for connection to said electrode means, for generating stimulus pulses at said output for delivery to said electrode means in the absence of detected heartbeat signals;

controllable means for controlling at least ones operating parameter of said demand generator means as a function of received parameter data;

parameter signal delivery means for controlled delivery of said parameter data to said controllable means, said parameter signal delivery means comprising (a) signal storage means for storage of digital signals and having a plurality of data locations; (b) receiving means for receiving said serially transmitted external signal; (c) connecting means for connecting said received signal serially to said signal storage means so that the data from said received signal is stored in respective different data locations; and (d) comparing means connected to said signal storage means for comparing in a predetermined manner the data in predetermined ones of said locations and for enabling said delivery of parameter data as a function of said comparison, thereby controlling said at least one operating parameter in accordance with said external signal.

2. The pacer as described in claim 1, wherein said signal storage means is a register, and said locations are register logic states, and said comparing means comprises circuitry having a plurality of fixed logic states corresponding to a predetermined access code, and said comparing means compares predetermined ones of said register logic states with said fixed logic states.

3. The pacer as described in claim 2, wherein said register has $n$ logic states, and wherein said predetermined ones of said register logic states are intermixed with the other of said register logic states.

4. The pacer as described in claim 1, wherein said comparing means compares predetermined pairs of said locations.

5. The pacer as described in claim 1, wherein said comparing means comprises a stored access data circuit having fixed logic states corresponding to access data, and wherein said comparing means comprises means for (i) comparing the data of selected ones of said signal storage locations with corresponding fixed logic states and (ii) comparing the data of selected ones of said signal storage locations with the data of selected other ones of said signal storage locations.

6. The pacer as described in claim 1, wherein said external signal is comprised of a train of width modulated pulses, and said receiving means and said connecting means operate to establish the logic state of each of said data locations as a function of the width of respective pulses in said external signal.

7. An implantable cardiac pacer adapted for connection to electrode means for delivering stimulus signals to and receiving signals from the heart, and being further adapted to be programmed in accordance with data from an external signal comprising a data word made up of a predetermined number of coded pulses, only some of said pulses carrying parameter data, comprising:
   a. demand generator means adapted for connection to said electrode means for generating stimulus pulses in the absence of detected heartbeat signals;
   b. controllable means for controlling at least one operating parameter of said demand generator means as a function of received parameter data;
   c. means for receiving said external signal, and means for decoding said pulses and storing signals representative of the data carried by each of said pulses;
   d. control output means for providing a plurality of parameter logic signals corresponding to said received signal, said control output means comprising means for comparing predetermined ones of said stored data signals with each other and means for enabling said parameter logic signals as a function of said comparison; and
   e. connecting means for connecting said parameter logic signals to predetermined circuit components of said demand generator means for parameter control of said generator means.

8. The pacer as described in claim 7 wherein some of said coded pulses carry comparison data corresponding to at least a portion of said parameter data, and wherein said means for decoding and storing comprises a register for holding said representative signals, said register having a plurality of logic states corresponding to said representative signals, and wherein said comparing means comprises
   first connecting means for connecting a first set of said register logic states to said comparing means, said first set corresponding to at least a portion of said parameter data, and
   second connecting means for connecting a second set of said logic states to said comparing means, said second set corresponding to said comparison data, whereby said comparing means compares said comparison data with said at least a portion of said parameter data.

9. The pacer as described in claim 8, wherein said external signal contains equal bits of parameter data and comparison data, and said comparing means compares each bit of parameter data with a corresponding bit of comparison data.

10. An implantable cardiac pacer in combination with electrode means for delivering stimulus signals to and receiving signals from the heart, and being further adapted to be programmed in accordance with data from an external signal comprising intermixed parameter data and access data, said pacer comprising:
   a. demand generator means connected to said electrode means for generating stimulus pulses and delivering same to said electrode means in the absence of detected heartbeat signals;
   b. controllable means for controlling at least one operating parameter of said demand generator means as a function of received parameter data;
   c. means for receiving and holding said external signal;
   d. a stored access data circuit having stored data in the form of predetermined logic states;
   e. control output means for providing a logic signal corresponding to said received signal, said control output means having means for decoding the access data in said received signal and comparing said decoded data with said stored data, and means for enabling said parameter logic signals as a function of said comparison; and
   f. connecting means for connecting said parameter logic signals to predetermined circuit components of said demand generator means for parameter control of said generator means.

11. The pacer as described in claim 10 wherein said external signal contains (i) parameter data and (ii) access data, and wherein said receiving and holding means comprises a register for holding said received signal, said register having a plurality of logic states, and wherein said control output means comprises
   first connecting means for connecting a first set of said register logic states to said comparing means, said first set corresponding to said access data, whereby said comparing means compares said access data with said stored data.

12. The pacer as described in claim 11, wherein said external signal is characterized by said parameter data and said access data being intermixed in time relation.

13. The pacer as described in claim 11, wherein said register contains a binary word having a predetermined number of bits, and the first and last logic states contain access bits when said external signal has been received.

14. The pacer as described in claim 11, wherein said external signal contains comparison data corresponding to at least a portion of said parameter data, and comprising second connecting means for connecting a second set of said register logic states to said comparing means, said second set corresponding to said comparison data, whereby said comparing means also compares said comparison data with said at least a portion of said parameter data.

15. The pacer as described in claim 14, wherein said external signal is characterized by said parameter data, access data and comparison data being intermixed.

16. A method of programming control of an implanted cardiac pacer adapted for delivering stimulus signals to and receiving signals from a heart, said pacer containing stored access logic states, comprising:
   a. transmitting an external signal coded to have parameter data and access data intermixed in a predetermined manner;
   b. receiving said external signal and storing same in the form of a binary data word in a storage register having a plurality of logic states, said binary word containing both parameter data bits and access data bits in intermixed form;
   c. comparing predetermined ones of said logic states with said access logic states, said predetermined logic states being those which store access data bits when said external signal has been received and stored without error; and
   d. controlling the operation of said pacer as a function of said received parameter data and as a function of said comparison.

17. The method as described in claim 16, comprising transmitting said external signal as a group of pulses, each pulse representing a bit, with a first predetermined number of parameter data bits and a second predetermined number of access data bits, and intermixing the time occurrence of said parameter data and access data bits.

18. The method as described in claim 17, wherein the parameter data and access data bits of said binary data word are stored in an order corresponding to the time occurrence of said group of pulses.

19. The method as described in claim 18, wherein the last bit of said external signal is an access data bit.

20. A cardiac power, having a circuit for producing pacing stimulus signals and circuitry for establishing pacer operating parameters, said pacer being adapted to be programmed by an external programming signal in the form of an intermixed multiple bit data word containing access and parameter data intermixed in a predetermined form, comprising:
   a. means for receiving said intermixed data word;
   b. means for determining the presence of a predetermined access code in predetermined bit positions within said intermixed data word;
   c. means for determining the parameter data content of said intermixed word; and
   d. means for controlling at least one of said operating parameters of said pacer as a function of said parameter data when said access code presence is determined.

* * * * *